United States Patent
Takizawa et al.

(10) Patent No.: US 7,635,979 B2
(45) Date of Patent: Dec. 22, 2009

(54) MAGNETIC RESONANCE IMAGING APPARATUS AND METHOD

(75) Inventors: Masahiro Takizawa, Kashiwa (JP); Tetsuhiko Takahashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 273 days.

(21) Appl. No.: 11/919,383

(22) PCT Filed: Apr. 25, 2006

(86) PCT No.: PCT/JP2006/308650

§ 371 (c)(1),
(2), (4) Date: Oct. 24, 2007

(87) PCT Pub. No.: WO2006/118110

PCT Pub. Date: Nov. 9, 2006

(65) Prior Publication Data

US 2009/0278535 A1    Nov. 12, 2009

(51) Int. Cl.
*G01V 3/00* (2006.01)

(52) U.S. Cl. .................................. 324/309; 324/307

(58) Field of Classification Search ......... 324/300–322; 600/410–435
See application file for complete search history.

(56) References Cited

U.S. PATENT DOCUMENTS

| | | | | | |
|---|---|---|---|---|---|
| 5,357,200 | A | * | 10/1994 | Kajiyama | 324/309 |
| 5,543,709 | A | * | 8/1996 | Kajiyama | 324/309 |
| 6,806,709 | B2 | * | 10/2004 | Markl et al. | 324/309 |
| 7,123,008 | B1 | * | 10/2006 | Damadian et al. | 324/309 |
| 7,375,521 | B1 | * | 5/2008 | Damadian et al. | 324/307 |
| 7,514,927 | B2 | * | 4/2009 | Herzka et al. | 324/318 |
| 2004/0245986 | A1 | * | 12/2004 | Kumai et al. | 324/307 |

FOREIGN PATENT DOCUMENTS

JP           06254064 A   *   9/1994

* cited by examiner

*Primary Examiner*—Brij B Shrivastav
*Assistant Examiner*—Dixomara Vargas
(74) *Attorney, Agent, or Firm*—Cooper & Dunham, LLP

(57) ABSTRACT

In performing the moving table imaging, an MRI apparatus and a method thereof are provided, which minimizes image degradation and reduces imaging time. When an image of a wide range of a test object is taken, the imaging is repeated while changing the gradient magnetic field intensity in a phase-encode direction, as well as changing the size of field of view FOV in the readout direction by changing the readout gradient magnetic field intensity in reading out the data, according to the phase-encode amount. In a part where the FOV is expanded, data acquisition frequency is lowered, and consequently, the total imaging time is reduced. The data sampling time may be changed along with the change of the FOV, and therefore, a process for achieving a unique matrix size in the readout direction is rendered unnecessary, and a spatial resolution can be maintained.

21 Claims, 15 Drawing Sheets

FIG.3
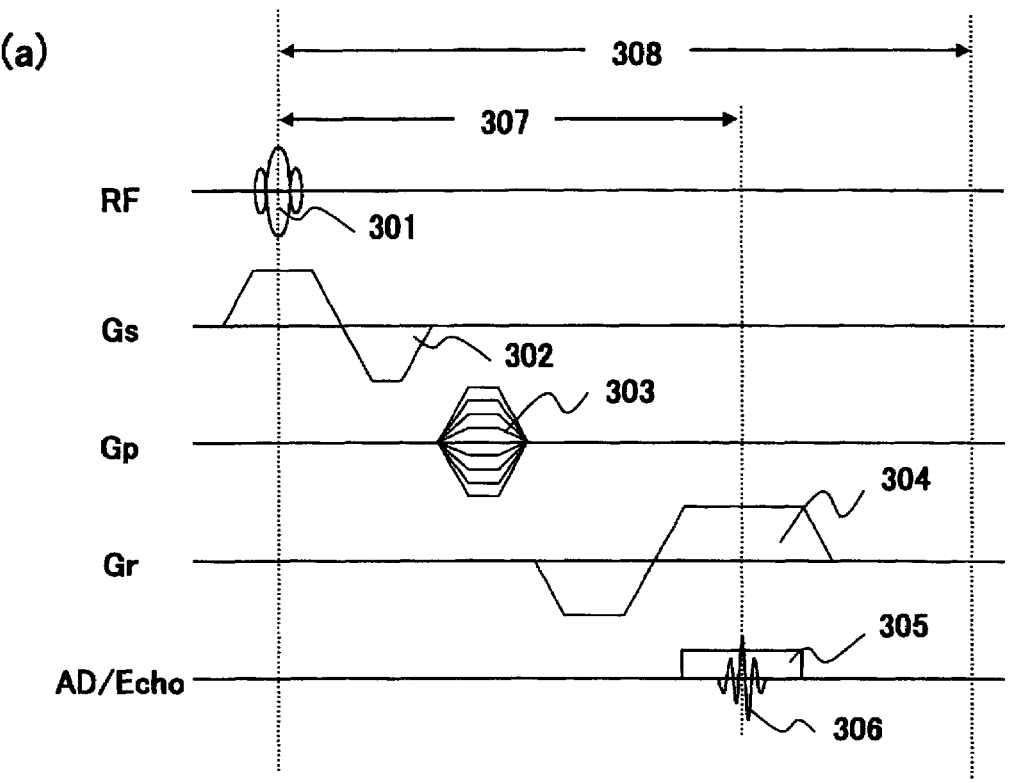
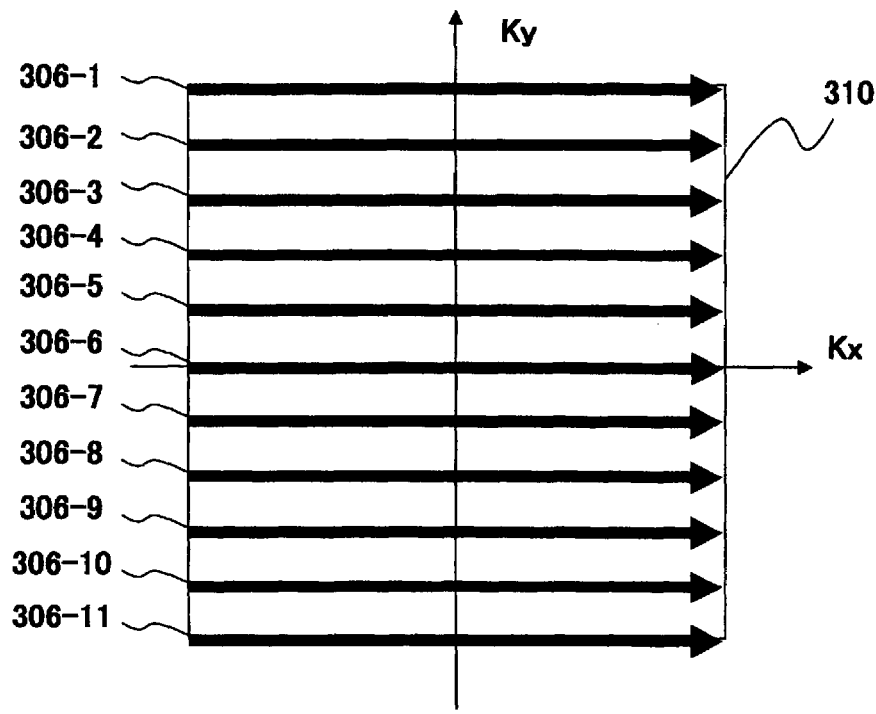

FIG.5
(a)
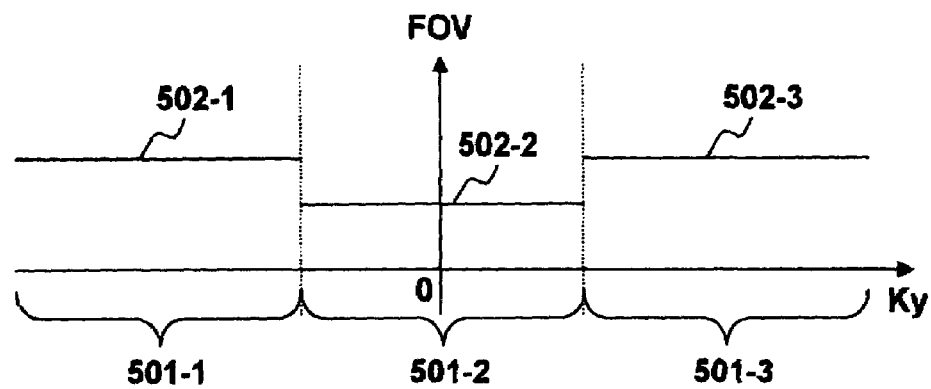
(b)
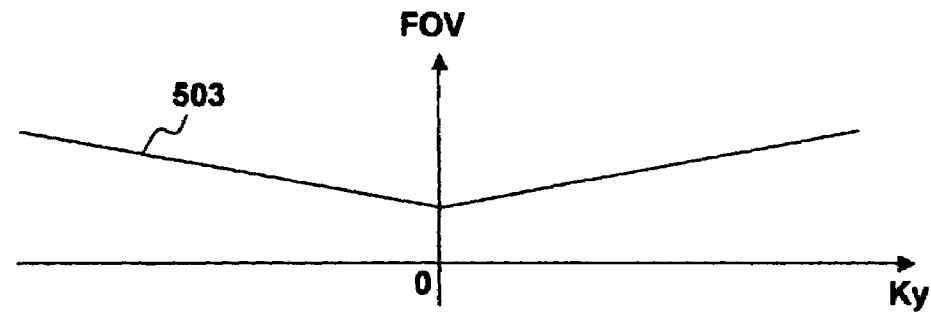
(c)
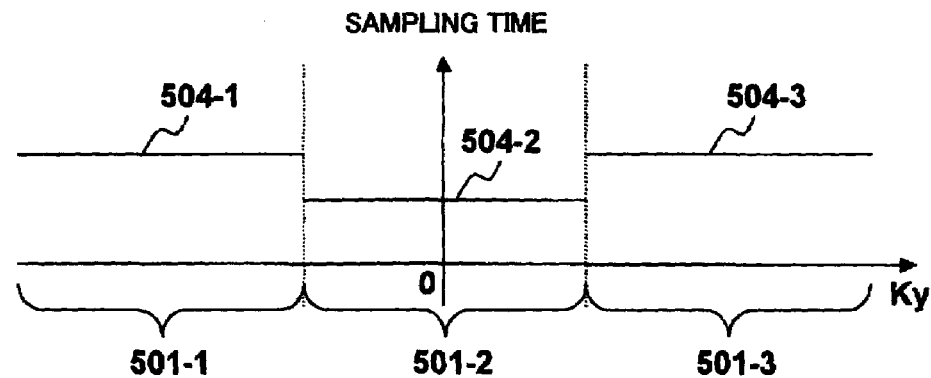
(d)
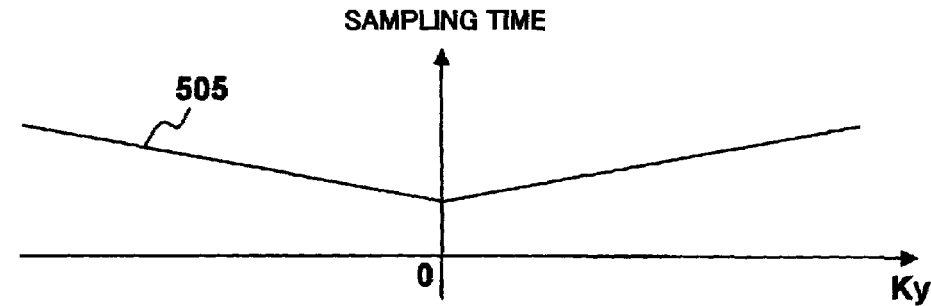

FIG.6
(a) 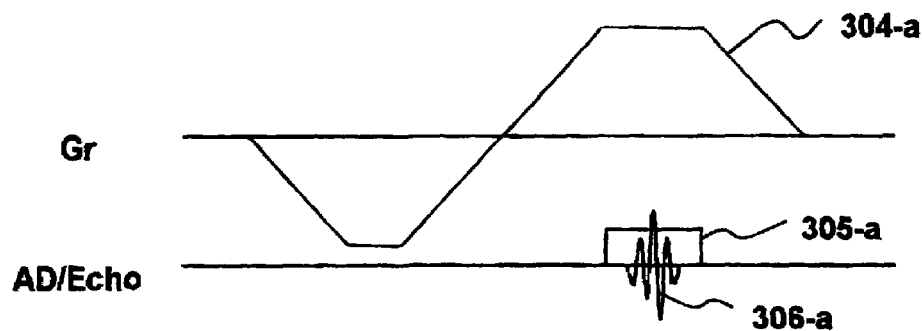
(b) 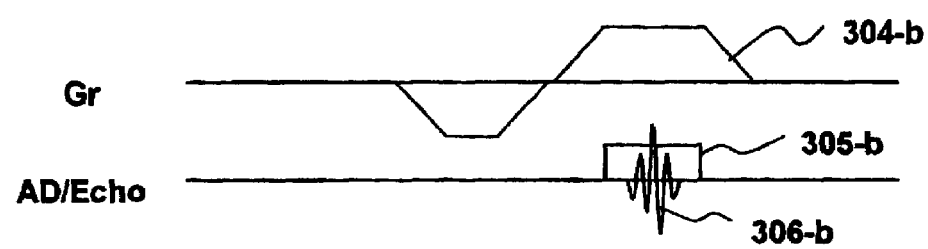
(c) 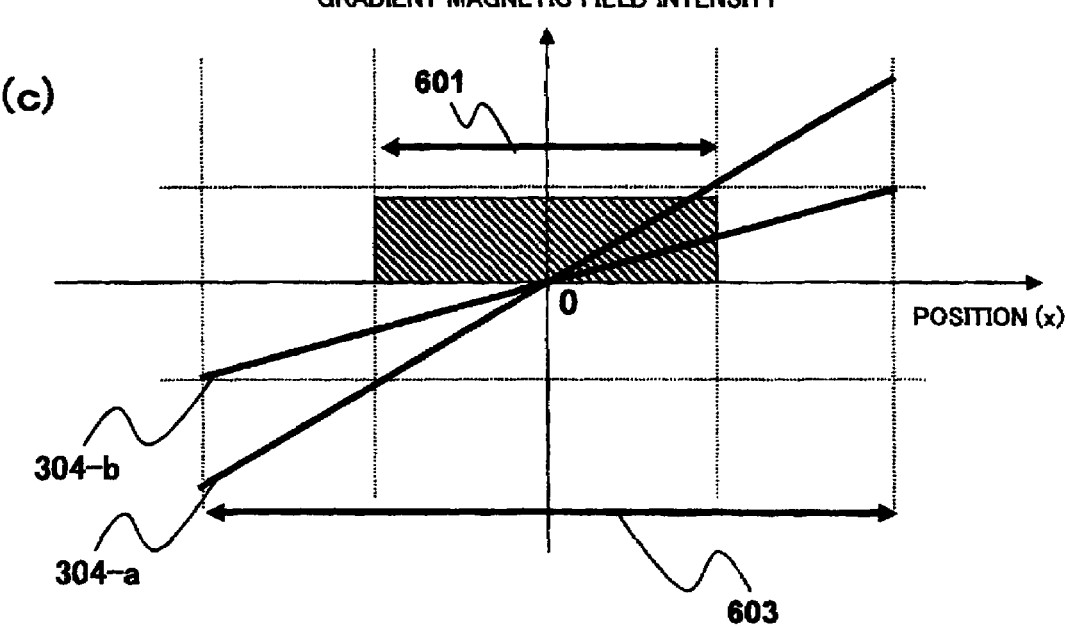

FIG.8
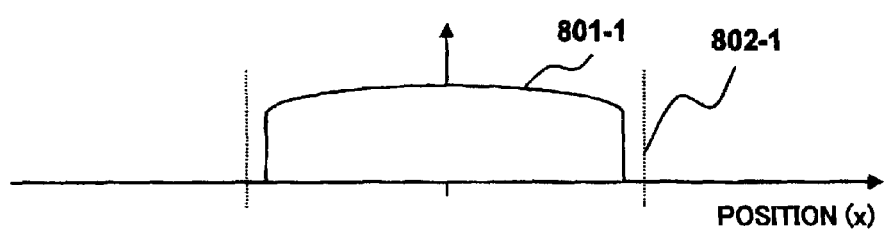
(a)
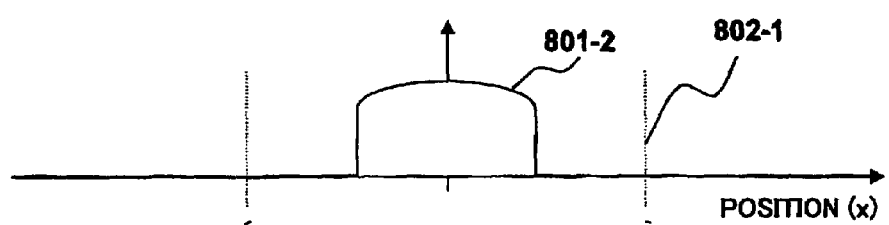
(b)
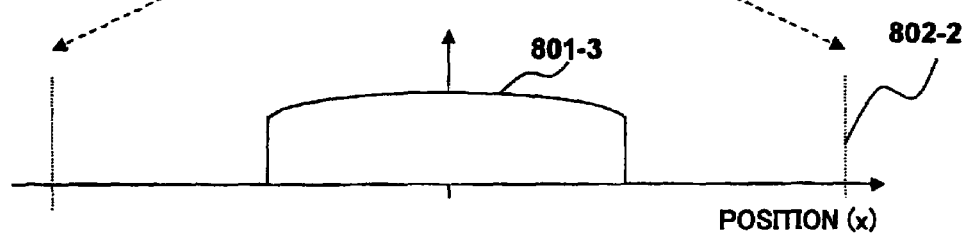
(c)
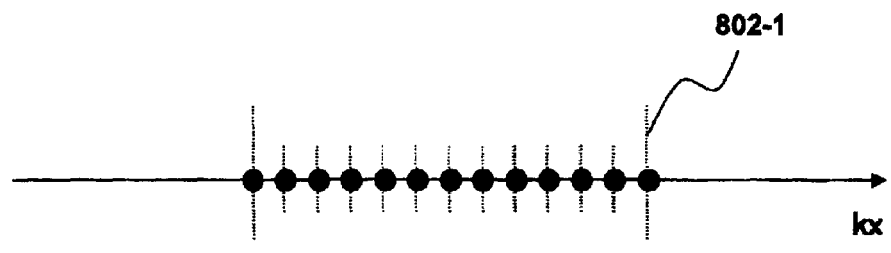
(d)
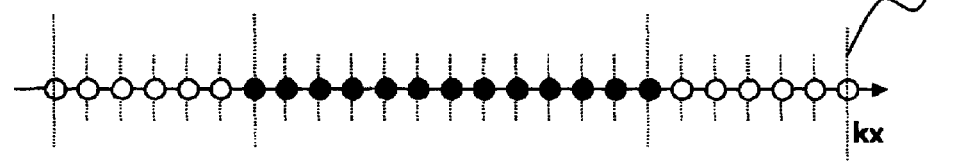
(e)

FIG.11 (a)
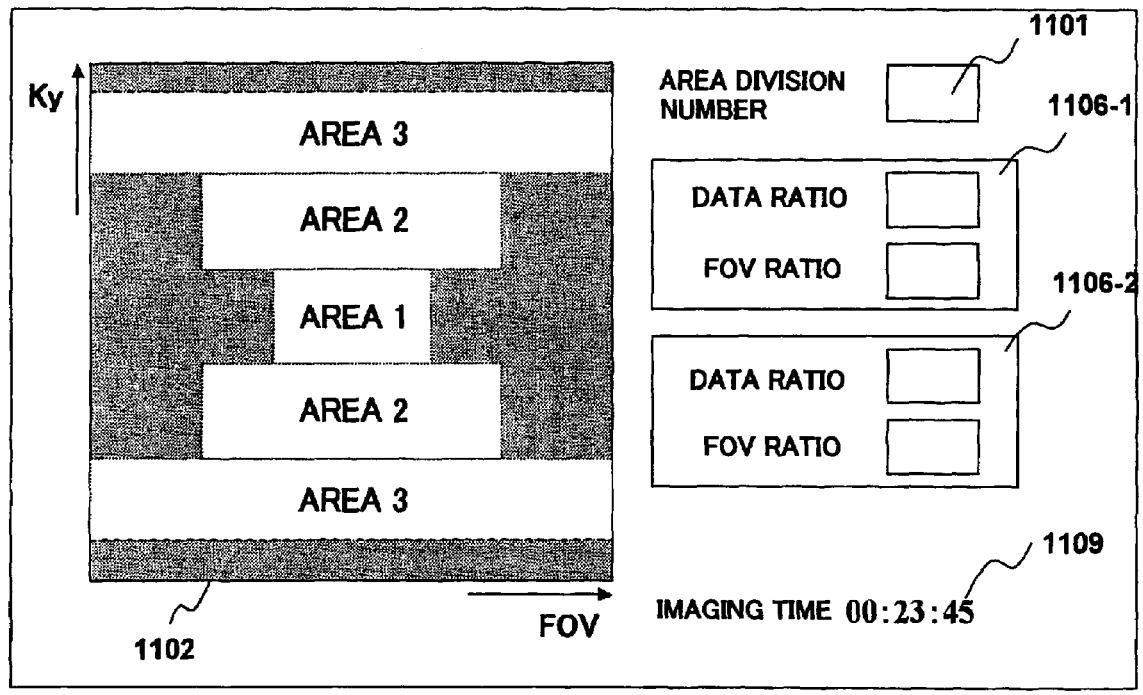
(b)
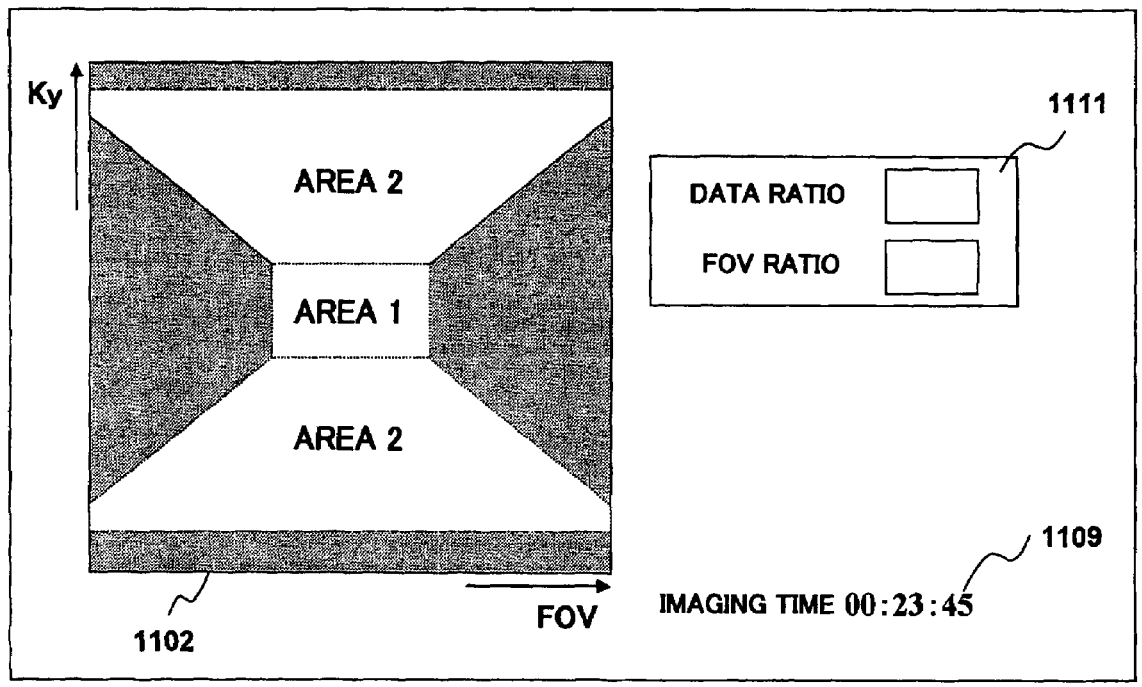

FIG.14
(a)
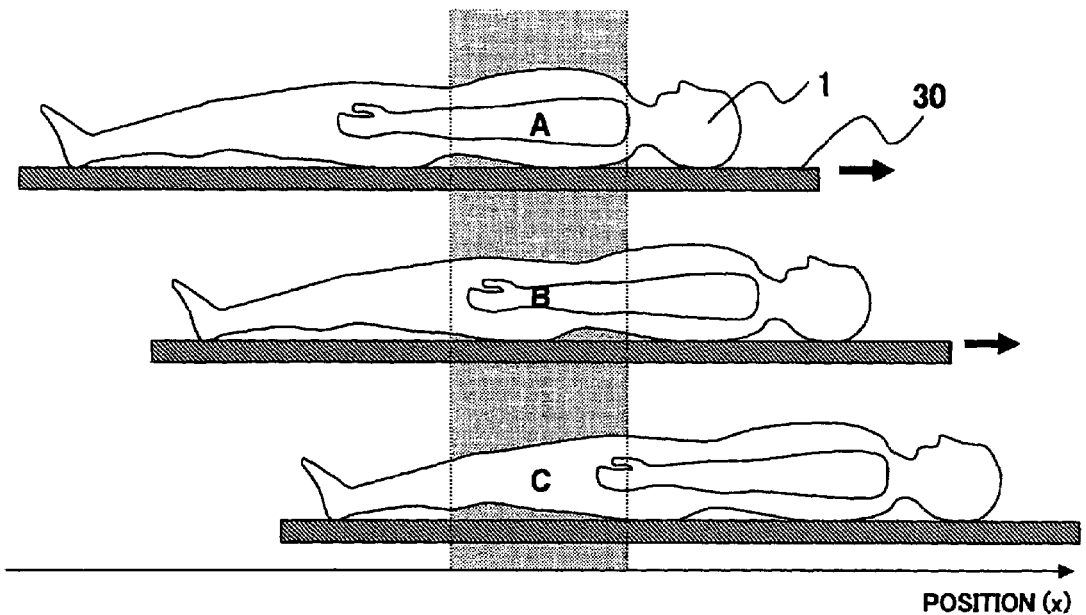
(b)
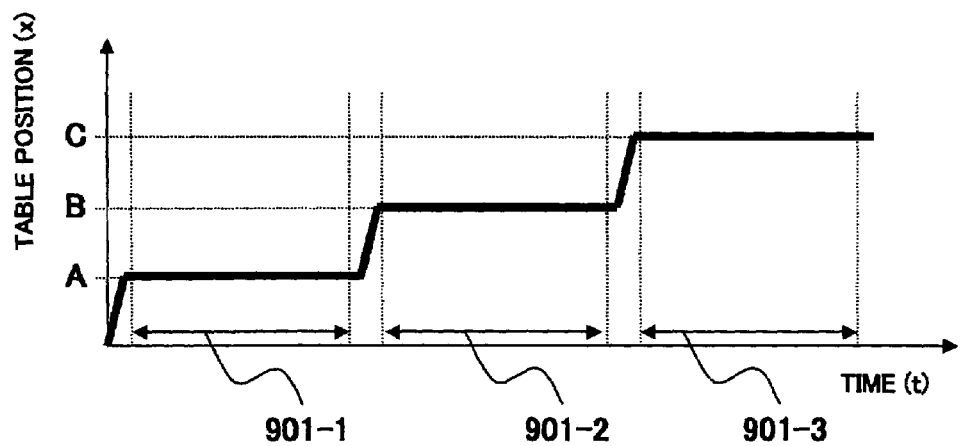
(c)
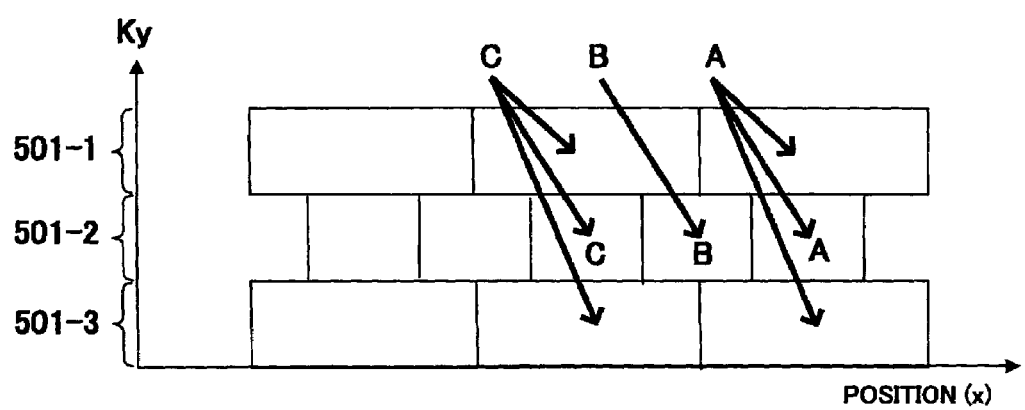

MAGNETIC RESONANCE IMAGING APPARATUS AND METHOD

TECHNICAL FIELD

The present invention relates to a magnetic resonance imaging apparatus (hereinafter, referred to as "MRI apparatus"), which utilizes a nuclear magnetic resonance phenomenon to obtain a tomographic image of an area to be examined of a test object. In particular, it relates to an MRI apparatus implementing a moving bed imaging, which takes an image while a table (bed) is moved with the test object placed thereon.

BACKGROUND ART

In the MRI apparatus, an imaging space is limited to an area having high static magnetic field uniformity within the static magnetic field space generated by a magnet, in order to obtain a high-quality image without any distortion or degradation of contrast. Even under the constraint as described above, there is proposed a method to obtain an image of an area wider than the uniform static magnetic field space, for example, a total body image, by moving the table on which the test object is placed while an image is taken (e.g., patent document 1). The patent document 1 discloses a method in which an imaging plane is set horizontally with respect to the table moving direction, and a readout direction is set to be the table moving direction, whereby an image of wider range can be taken within a relatively short time.

[Patent Document 1]
Japanese Unexamined Patent Application Publication (Translation of PCT application) No. 2004-537301

DISCLOSURE OF THE INVENTION

Problem to be Solved by the Invention

In the technique described in the patent document 1, an imaging time is reduced compared to a conventional moving table imaging, but further reduction of the imaging time is still expected. In addition, even under such condition, it is important that the image is not degraded.

In view of the situation above, the present invention relates to an MRI apparatus and method, enabling a reduction of the imaging time with minimum image degradation, in performing the moving table imaging.

Means to Solve the Invention

In order to achieve the above object, the MRI method and apparatus according to the present invention changes a data acquisition condition (data readout condition) in the readout gradient magnetic field direction, according to a phase-encode amount that is applied at the time of acquiring an echo signal, thereby achieving a reduction of the imaging time.

In other words, the MRI method according to the present invention includes, a transfer step for moving the test object by a transfer means in such a manner that a wide imaging range of the test object passes through the static magnetic field space, an echo data acquisition step for performing an imaging according to a nuclear magnetic resonance and obtaining echo data corresponding to one or more phase-encode, a repetition step for repeating the transfer step and the echo data acquisition step, and an image reconstruction step for reconstructing an image of the wide imaging range by using multiple echo data obtained in the repetition step, wherein, a readout condition for reading out the echo data of at least one phase-encode is controlled to be different from the readout condition of the echo data of another phase-encode in the repetition step.

An MRI apparatus according to the present invention includes, a static magnetic field generation means for generating a static magnetic field in a space where a test object is placed, a magnetic field generation means for generating a gradient magnetic field and an RF magnetic field in the space, a receiving means for receiving a nuclear magnetic resonance signal generated from the test object on which a readout gradient magnetic field is applied, a signal processing means for performing an image reconstructing computation by using the nuclear magnetic resonance signal, a transfer means for placing the test object thereon and moving the test object into the space, and a control means for controlling operations of the magnetic field generation means, the receiving means, the signal processing means, and the transfer means, which obtains an image of a wide imaging range of the test object by moving the transfer means, wherein the control means is provided with a means for controlling the readout condition so that the a readout condition of echo data is made different according to a phase-encode.

Variation of the data readout condition may include, for example, a change of a size of FOV (field of view) in the readout direction and a change of a sampling time.

EFFECT OF THE INVENTION

By changing the readout condition of the echo data according to the phase-encode, it is possible, for example, to reduce a data acquisition frequency as for any component among the measurement space data, and reduce an imaging time as a whole. Since the imaging condition in the readout direction is changed, there is no restriction due to a necessity for preventing aliasing. Furthermore, since a control is exercised in accordance with the phase-encode, it is possible to minimize image degradation.

BEST MODE FOR CARRYING OUT THE INVENTION

Hereinafter, an embodiment of the present invention will be explained with reference to the accompanying drawings. FIG. 1 is a diagram showing an overview of the MRI apparatus to which the present invention is applied. This MRI apparatus is provided with a static magnetic field generation unit 2, a gradient magnetic field generation unit 3, a transmitting unit 5, a receiving unit 6, a signal processing unit 7, a sequencer 4, a central processing unit (CPU) 8, and a table 30 to lay a test object 1 thereon.

The static magnetic field generating unit 2 generates a uniform static magnetic field in a body axis direction or in a direction orthogonal to the body axis in the space surrounding the test object 1, employing a magnetic field generation means such as a permanent magnet system, a normal conducting system, or a superconducting system. A table drive mechanism 31 controls the table 30, so as to transfer the test object 1 being laid thereon, within the static magnetic field space formed by the static magnetic field generation unit 2.

The gradient magnetic field generation system 3 is made up of the gradient magnetic field coils 9 wound in the three axial directions X, Y, and Z, and a gradient magnetic field power source 10 that drives each of the gradient magnetic field coils, and generates gradient magnetic fields Gs, Gp, and Gr in a desired direction within the static magnetic field space, by driving the gradient magnetic field power source 10 for each of the gradient magnetic field coils, in response to a command from the sequencer 4. According to the way how to apply these gradient magnetic fields, an imaging section (slice plane) of the test object 1 is selected, and positional information (phase-encode, frequency-encode, and the like) can be added to the nuclear magnetic resonance signal (echo signal) generated from the test object 1.

The sequencer 4 is operated by the control of the CPU 8, and controls the transmitting unit 5, the gradient magnetic field generation unit 3, and the receiving unit 6, so that an RF magnetic field pulse (RF pulse) and a gradient magnetic field pulse are applied repeatedly, according to a predetermined pulse sequence.

The transmitting unit 5 irradiates an RF pulse so as to cause a nuclear magnetic resonance in a nuclear spin of each atomic element constituting a living tissue of the test object 1, and the transmitting unit is made up of an RF oscillator 11, a modulator 12, an RF amplifier 13, and an RF coil 14a for transmitting. An RF pulse outputted from the RF oscillator 11 is subjected to an amplitude modulation by the modulator 12 at a time according to a command from the sequencer 4, and the RF pulse being subjected to the amplitude modulation is amplified by the RF amplifier 13. Then, the pulse is supplied to the RF coil 14a placed in proximity to the test object 1, whereby an RF pulse, i.e., an electromagnetic wave is irradiated on the test object 1.

The receiving unit 6 detects an echo signal emitted by the nuclear magnetic resonance in the nuclear spin of each atomic element constituting the living tissue of the test object 1, and the receiving unit is made up of an RF coil 14b for receiving, an amplifier 15, and a quadrature phase detector 16, and an A/D converter 17. A response electromagnetic wave (NMR) from the test object that is induced by an electromagnetic wave irradiated from the RF coil 14a for transmitting is detected by the RF coil 14b arranged in proximity to the test object 1, and the NMR signal is amplified by the amplifier 15, and then, divided into orthogonal two-series signals by the quadrature phase detector 16 at the time directed by the sequencer 4. Thereafter, each signal is converted into a digital amount by the A/D converter, and transferred to the signal processing system 7.

The signal processing unit 7 includes an external storage unit such as a magnetic disc 18 and an optical disc 19, and a display made up of CRT and the like. When data from the receiving unit 6 is inputted into the CPU 8, the CPU 8 executes a processing such as a signal processing and an image reconstruction, and displays a resulting tomographic image of the test object 1 on a display, as well as recording the image in the external storage unit such as the magnetic disc 18.

The CPU 8 constitutes a part of the signal processing unit 7, and also functions as a controller for controlling the entire apparatus. In other words, it exercises control over the imaging via the sequencer 4 described above and control over the move and pause of the table via the table drive mechanism 31, thereby controlling the table moving speed so that the table moving speed conforms to the imaging speed controlled by the sequencer 4. An operation part 25 is provided to input various control information of the apparatus and information necessary for the processing carried out in the signal processing unit 7, and it includes a track ball or a mouse 23, a keyboard 24, and the like. The operation part 25 is arranged in proximity to the display 20, and an operator controls various processes of the apparatus interactively via the operation part 25, while viewing the display 20.

Next, a moving table imaging will be explained, which is executed in the MRI apparatus having the configuration above. FIG. 2 includes illustrations showing one embodiment of continuous moving table imaging that is executed by the MRI apparatus according to the present invention. In this embodiment, an imaging plane is set horizontally with respect to the table 30, and the imaging is performed while moving the table 30 in the body axis direction (H-F direction) of the test object 1. FIG. 2(*a*) and FIG. 2(*b*) are illustrations showing a relationship between the moving direction of the table and the imaging plane. FIG. 2(*c*) and FIG. 2(*d*) are illustrations showing data arrangement after the echo signals being measured are subjected to the Fourier transform in the readout direction.

In the present embodiment, an image is continuously taken while the table is moved with respect to the apparatus, in the state where the imaging plane is fixed to the device coordinate. Accordingly, when viewed from the coordinate of the test object 1, the imaging planes 201-1 and 201-2 are moved in the reverse direction of the table moving direction, and consequently, data for a wide viewing field can be obtained.

A pulse sequence for the imaging is not particularly limited, and a publicly known high-speed pulse sequence may be employed. By way of example, a pulse sequence of 2D gradient echo system is shown in FIG. 3. In the figure, RF, Gs, Gp and Gr represent respectively, RF pulse, slice gradient magnetic field, phase-encode gradient magnetic field, and application timing of frequency-encode gradient magnetic field. AD/Echo represents an echo signal and the sampling time thereof. In this gradient echo pulse sequence, an RF pulse 301 having a frequency that excites a nuclear spin of the test object is applied together with a selection gradient magnetic field 302 for selecting an imaging plane, and next, the gradient magnetic field 303 in the phase-encode direction is applied. In addition, while applying the readout gradient magnetic field 304, an echo signal 306 is measured within the sampling time 305, after a lapse of the echo time 307 from the application of the excitation RF pulse 301. In the embodiment as shown in FIG. 2, the COR plane is set as the imaging plane. Therefore, the slice direction (z-direction) is set as a direction orthogonal to the table moving direction, the phase-encode direction (y-direction) is set as the left and right direction of the test object, and the readout direction (x-direction) is set as the table moving direction.

Such sequence as described above is repeated every predetermined repetition pulse 308, while the phase-encode is varied. The phase-encode is determined by the product of the intensity of the phase-encode gradient magnetic field 303 and the application time, and in general, only the intensity is changed. In the case of imaging without moving the table, at the time when the data of entire phase-encode is obtained, the data becomes k-spatial data 310 that is required for reconstructing one image, as shown in FIG. 3(*b*). However, in the case of the moving bed imaging where an image is taken while the table is moved, the readout gradient magnetic field is applied in such a manner as being displaced in the table moving direction (readout direction) with respect to each echo. Therefore, as shown in FIG. 2(*c*), the data items 202-1 to 202-8 obtained by subjecting the echoes to the Fourier transform in the readout direction, are displaced one from the other in the x-direction. However, after the data 202-8 is measured, the phase-encode amount is resumed to be the same as the data 202-1, and then, the data items 202-9 to 202-16 are obtained while the phase-encode is changed, i.e., the phase-encode is changed recursively, whereby the data is rendered to be continuous with respect to each phase-encode. Consequently, as shown in FIG. 2(*d*), the data items 203-1 to 203-8 being continuous in the x-direction are obtained. Those data items are further subjected to the Fourier transform in the phase-encode direction, whereby a reconstructed image of a wide range, for example, an image of the total body, can be obtained.

In the MRI apparatus according to the present invention, when such moving table imaging is executed, a data readout condition is changed in accordance with changing the phase-encode, thereby reducing the imaging time. The data readout condition includes, specifically, the intensity of the readout gradient magnetic field, a sampling time, and a sampling band. These conditions are changed so that the data measuring frequency is lowered according to the phase-encode amount.

Hereinafter, a first embodiment of the readout condition control according to the phase-encode will be explained. In the first embodiment, in the continuous moving table imaging, the measuring is divided into multiple blocks according to the application amount of the phase-encode gradient magnetic field pulse (phase-encode amount), and the size of an FOV in the readout gradient magnetic field direction is changed with respect to each block.

FIG. 4 includes diagrams showing a control procedure of the CPU (controller) 8 according to the first embodiment. FIG. 4a shows an overview of the procedure, and FIG. 4b shows the details of the procedure. In the first embodiment, the continuous moving table imaging is selected initially. When a pulse sequence for the imaging and the parameters thereof (phase-encode number, echo time, and repetition time) are set, a measuring condition is set in step 101, as illustrated. In setting the measuring condition, a user sets parameters for controlling the readout condition (step 401), and setting of the FOV according to the phase-encode amount, setting of echo acquisition order, and calculation of the table moving speed and the imaging time, are executed (steps 402 and 403). Setting of the parameters will be described in detail in the following.

By way of example, as shown in FIG. 5(a), in setting of a field of view (FOV) according to the phase-encode amount, the measurement space (k-space) is divided into multiple blocks (three in the figure) 501-1, 501-2, and 501-3 according to the phase-encode amount. When the size of the field of view (FOV) 502-2 in the readout direction of the block 501-2 being a low spatial frequency area is set as a standard, the FOV sizes 502-1 and 502-3 in the readout direction respectively in the blocks 501-1 and 501-3 being the high spatial frequency area are set larger than the standard, for example, twice as large. Making changes of the FOV size in the readout direction can be implemented by changing the gradient magnetic field intensity in the readout direction.

Specifically, since there is a relationship between the field of view size FOV and the gradient magnetic field intensity Gr as shown in the following formula;

$$Gr = BW/(\gamma \cdot FOV) \quad (1)$$

(BW represents a sampling band, and $\gamma$ represents a gyromagnetic ratio)

If the sampling band is constant, the gradient magnetic field intensity Gr in the readout direction is inversely proportional to the FOV. Therefore, if the gradient magnetic field intensity Gr is made to half, the FOV can be made twice as large. The situation above is shown in FIG. 6. FIG. 6(a) and FIG. 6(b) illustrate only the readout gradient magnetic field 304, the sampling time 305, and the echo signal 306 of the pulse sequence as shown in FIG. 3. The readout gradient magnetic field Gr is made to half in FIG. 6(b), when FIG. 6(a) is taken as the standard. As shown in FIG. 6(c), when the gradient magnetic field intensity is made to half (304-b) relative to the gradient magnetic field intensity 304-a having the range 601 as the FOV where the test object exists, an enlarged FOV size 603 can be obtained as the data range in the readout direction, within the same gradient magnetic field intensity range as the gradient magnetic field intensity 304-a. Therefore, in measuring the blocks 501-1 and 501-3 in the high spatial frequency area, the readout gradient magnetic field is controlled as shown in FIG. 6(b), whereby each FOV size of the blocks 501-1 and 501-3 is twice as large as the FOV size of the block 501-2.

Along with changing the FOV size in the readout direction according to the phase-encode amount, the measuring frequency becomes different according to the phase-encode amount of the echo signal, and accordingly, the order for measuring the echo signal is configured (step 402). FIG. 7 shows a relationship between the FOV size and the order for acquiring data. FIG. 7 shows hybrid spatial data which is obtained by subjecting the data to the Fourier transform in the x-direction, and in the figures, a framed rectangle represents one data, and a black dot at the center thereof represents a magnetic field center.

FIG. 7(a) shows the case where a general continuous moving table imaging is performed, and since the FOV size is fixed in this case, data of each phase-encode is measured periodically at regular intervals. Assuming that there is no addition of data, the table moving speed is configured in such a manner that the time period when the table has moved in the x-direction width of the FOV range corresponds to the measuring time of the entire phase-encode.

On the other hand, for example, in the case where the FOV size of the high-spatial frequency components (blocks 501-1, and 501-3) is made to be twice as large as the FOV size of the low-spatial frequency component (501-2) (reference), as shown in FIG. 7(b), the measuring order is controlled so that the block 501-2 is measured twice while the blocks 501-1 and 501-3 are measured once. The table moving speed in the case above is configured in such a manner that the time period when the table is moved in the FOV width in the readout direction of the block having the largest FOV size corresponds to, or to be longer than, the time required for one-time measuring of the high-spatial frequency components and two-time measuring of the low-spatial frequency component (step 403).

Accordingly, without missing data, the low-spatial frequency component can be measured with a high frequency. Basically, as for the measuring order of the phase-encode, the measurement frequency is made high in the area where the set FOV size is the smallest, and the measurement frequency is made lower as the set FOV size is made larger. These settings above can be determined uniquely if the number of divided areas and the FOV size are decided, and therefore, it can be automatically configured in step 402.

Hereinafter, there will be explained a way how to obtain an optimum table moving speed, when data is acquired by changing the FOV size. Here, there is considered a case as shown in FIG. 7(b), where the area of measurement space is divided into to two areas, a low spatial frequency area (area 1) and a high spatial frequency area (area 2), and different FOV sizes are assigned to the areas respectively.

In a general continuous moving table imaging, when the repetition time of the sequence is expressed by TR, the count of phase-encode being acquired is expressed by N, and the data point in the readout direction is expressed by X, the table moving speed V has to satisfy the following:

$$V \leq \frac{X}{TR \times N} \quad \text{[FORMULA 1]}$$

On the other hand, when an acquisition ratio (%) of the area 1 relative to the data size in the phase-encode direction is expressed by $R_N$ ($0 \leq R_N \leq 100$), and the increase ratio of the FOV size is expressed by $R_x$ ($1 \leq R_x$), the table moving speeds $V_1$ and $V_2$ in the respective areas are expressed as the following, relative to the table moving speed V in the case where the area is not divided:

$$V_1 \leq V \times \frac{200}{100 + R_N} \quad \text{[FORMULA 2]}$$
$$V_2 \leq V \times \frac{100 \times R_x}{100 + R_N}$$

By way of example, when the area 1 is set to half of the data size in the phase-encode direction ($R_N=50$), and the FOV size of the area 2 is set to be twice as large ($R_x=2$), the moving speeds are expressed as the following:

$$V_1 \leq V \times \frac{200}{150} \quad \text{[FORMULA 3]}$$
$$V_2 \leq V \times \frac{200}{150}$$

In this case, speedup of 1.33 times can be achieved, compared to the case where the FOV size is not changed. In addition, a limit of the table moving speed may be different between the two areas, depending on the settings of $R_N$ and $R_x$, but in order to move the table continuously, it is preferable to select the lower speed, $V_1$ or $V_2$, for the setting.

As thus described, once the settings are configured for the FOV size according to the phase-encode amount and for the measuring conditions including the data measuring order and the table moving speed, measuring of data is started based on the configured conditions (FIG. 4: step 102, step 404). In measuring the data, for example, on the basis of the pulse sequence as shown in FIG. 3, the aforementioned conditions are added thereto, and measuring of an echo signal is repeated while the table is moved (step 405). In the present embodiment, the measurement is repeated under the same readout condition in the same phase-encode area being set, i.e., while changing the phase-encode within the same phase-encode area with the same FOV. When the phase-encode area is changed, the readout condition is also changed, and then, the measurement is repeated (step 406).

When the measurement of the entire imaging area as a measurement target of the test object is completed, or all the echo signals necessary for reconstructing an image are acquired, the image is reconstructed by using the echo signals being obtained (step 408). However, in the case above, since the FOV size is different depending on the phase-encode amount, it is necessary to execute a processing to make a matrix size uniform, in the first place (step 103, 407).

With reference to FIG. 8, the processing to achieve the uniform matrix size will be explained. This processing is to obtain a uniform spatial resolution of data, and it is applicable to the measurement space data before the Fourier transform, or it is also applicable to the data after the Fourier transform.

FIG. 8 (*a*) to (*c*) illustrate the processing for the data after the Fourier transform, and FIG. 8 (*d*) to (*e*) illustrate the processing for the measurement space data.

FIG. 8(*a*) shows a signal intensity profile which is obtained by subjecting one row of data (trajectory) obtained with a basic FOV to one-dimensional Fourier transform. Here, data having the data range 802-1, which is a little larger than the test object area 801-1, is obtained. FIG. 8(*b*) illustrates a case where the FOV is set to be twice as large as the basic size of FIG. 8(*a*). Since only the FOV size is changed, the data range 802-1 is the same as the basic FOV size as shown in FIG. 8(*a*), but the test object area 801-2 is relatively reduced. The processing to achieve a uniform matrix size is a processing to expand the reduced data shown in FIG. 8(*b*), to the data as shown in FIG. 8(*c*), and a publicly known method can be utilized, such as the spline interpolation or the interpolation using Sinc function. When the data is expanded as thus described, not only the test object area 801-2 but also the data range 802-1 is expanded simultaneously to become the data range 802-2. Accordingly, if the test object area is continuous in the x-direction, data of much wider range can be obtained.

FIG. 8(*d*) shows a data row in the measurement space obtained by subjecting the data shown in FIG. 8(*b*) to the inverse Fourier transform, and black spots in the figure represent the data points being measured. Interpolation of such measurement space data as described above may be performed by embedding the outside of the data range 802-1 with zero data, and expanding the data range as shown in FIG. 8(*d*). Thereafter, by subjecting the data 802-2 to the inverse Fourier transform, an expanded data string similar to the data shown in FIG. 8(*c*) can be obtained. The data as to which the processing for achieving the uniform matrix size is completed is arranged in the data space for the image reconstruction.

The data measurement (step 404) to the data reconstruction (step 407) described above are repeated until reaching the end position of the imaging target range (step 104). After the data of the entire range is collected eventually, the data arranged in ky-x space (hybrid space) is subjected to the Fourier transform in the y-direction, for instance, whereby an image of the entire imaging target can be obtained (step 105, 408). As shown in FIG. 4, the image reconstruction step may be executed after the data of entire imaging range is obtained. Alternatively, the image reconstruction is performed every time when the data of entire phase-encode is obtained, with respect to each FOV, and thereafter the images of respective FOV may be combined.

In the present embodiment as explained above, the imaging is divided into several blocks according to the phase-encode amount, and imaging is performed in the FOV sizes respectively different in the readout direction. Therefore, the measuring frequency (echo data acquisition frequency) can be made high in the low spatial frequency component, and the measuring frequency is made low in the high spatial frequency component, whereby the image degradation can be minimized and the imaging time can be reduced.

By taking an image as described above, an image used for morphology diagnostics, which is generally obtained by the MRI, can be obtained without degradation of low spatial frequency information that is necessary for obtaining a shape of the test object. The degradation may include a spatial resolution degradation, increase of image distortion when the field of view FOV is enlarged, and the like.

In the above preferred embodiment, there has been explained a case where the FOV size to obtain a high spatial frequency component is made twice as large as the FOV size to obtain a low spatial frequency component. However, as shown in FIG. 7(*c*), for example, the FOV size to obtain the high spatial frequency component may be three times larger, and it is possible to optionally set the size to be changed, taking the image quality into account.

In the preferred embodiment as described above, the imaging is divided into three blocks according to the phase-encode amount (the measurement space is divided into two areas), and FOV sizes respectively different are set in the blocks. However, the division number may be optionally decided. Furthermore, as shown in FIG. 5(b), the FOV size 503 may be continuously changed according to the change of the phase-encode amount.

In the preferred embodiment as described above, there has been explained a case where the phase-encode amount is continuously changed. However, in the present embodiment, there is no restriction as to the order of applying the phase-encode, and therefore, an optional order or a change of the order in stepwise is possible, so that the present invention is the most effective.

In the continuous moving table imaging, the FOV also moves in the reverse direction of the table moving direction. Therefore, the data acquisition order is subject to constraints of the table moving speed. Therefore, in order to keep the table moving speed constant, it may be necessary to change the order for applying the phase-encode as described above, to change the FOV size along with the table moving, or to execute a process for adding the data items which are overlapping in the readout direction.

Hereinafter, as a modified example of the first embodiment, FIG. 9 shows an example where the FOV size is changed along with the table moving, or the data addition is executed. For ease of explanation, FIG. 9 shows an example where the phase-encode step is set to be 6 (six), and the data readout condition is sequentially changed. As illustrated, when the table moving speed is constant, while the data is measured in the phase-encode steps 1 to 6, the magnetic field center in the test object coordinate is moved as represented by the black spots in the figure. The phase-encode steps 2 to 5 are repeated after the data in the phase-encode step 6 is measured until the data in the phase-encode step 1 is measured again. Here, since the measurement is repeated at the same intervals in the both end phase-encode steps 1 and 6, the table moved amount in these steps is constant and therefore the FOV can be the same. However, in the phase-encode steps 2 to 5, the interval between the times when the measurement of the same phase-encode is performed (the table moved amount during that time) is not constant. Therefore, in order to avoid overlaps of the data, the imaging FOV size has to be cyclically changed every repetition of the measurement. On the other hand, if the FOV size is fixed with respect to each phase-encode, the data items in the same phase-encode may overlap one on another, as shown by the diagonally shaded area in the figure. In this case, the overlapping parts of the data items are subjected to the addition process. By applying the change as described above, it is possible to achieve an effect that the image degradation is minimized and the imaging time can be reduced, similar to the above embodiment.

Next, with reference to FIG. 10, a second embodiment of the readout condition control in the present invention will be explained, in which the measuring frequency is lowered in the low spatial frequency component, and the measuring frequency is heightened in the high spatial frequency component.

Also in this embodiment, the imaging is divided into three blocks 1001-1, 1001-2, and 1001-3, similar to the first embodiment. In this example here, when the FOV size of the high spatial frequency blocks 1001-1 and 1001-3 are used as the reference, the FOV size of the low spatial frequency block is made three times larger than the reference. Therefore, as shown in the figure, the measuring order is configured in such a manner that the measuring frequency in the low spatial frequency block is set to be one-third of the measuring frequency of the high spatial frequency blocks 1001-1 and 1001-3. As for this measuring order, the phase-encode is continuously changed within the same block, but this continuity is not always kept between the blocks, and this point is also different from the first embodiment.

In the present embodiment, the FOV size of the low spatial frequency area is set to be large, and therefore, the imaging time can be reduced similar to the first embodiment. Specifically, for example, when a ratio of the high spatial frequency block is 50% of the data and the measuring frequency is one-third, the speed is improved 1.33 times higher (time reduction effect of 75%) provided that the table speed is constant. If the table speed is variable, it is possible to obtain the time reduction effect of approximately 66% (=(50+50/3)÷100). In the present embodiment, the frequency for updating the high spatial frequency area is high, it is effective in the imaging targeted for blood vessel structure, such as angiography (MRA), for instance.

As thus described, in the present invention, it is possible to optionally configure settings according to a target imaging, which frequency component of the measurement space the readout condition should be changed, in other words, in which frequency component, the measuring frequency should be heightened or lowered. The frequency component in which the measuring frequency is set to be high may be selected in accordance with a rough ratio of the diagnostic target structure in the reconstructed image. By way of example, when a change in a fine structure is diagnosed, it is preferable to update highly frequently the high frequency component. On the contrary, when it is sufficient to diagnose the entire structure to some extent, it is preferable to update highly frequently the low frequency component.

Next, a preferred embodiment of a parameter setting screen will be explained, in order to execute the above embodiment. The parameter setting screen is displayed on the display 20, so that a user sets a readout condition when the readout condition is controlled according to the phase-encode amount. One example of the parameter setting screen is shown in each of FIG. 11(a) and FIG. 11(b).

The parameter setting screen as illustrated in FIG. 11(a) includes parameter input parts 1101, 1106-1, and 1106-2, which accept an input of parameters such as an area division number of the measurement space, data ratio and FOV ratio of each block being divided, and a result display part 1102 which displays a result of the parameter settings in a form of the measurement space. Firstly, the user sets the division number of the measurement space in the parameter input part 1101. Accordingly, in the result display part 1102, there is displayed the measurement space being partitioned into the number of areas, corresponding to the division number being set. Furthermore, in the parameter input parts 1106-1, 1106-2, and so on, data ratio (1 to 100%) and the FOV ratio of the measurement space of each of the areas 1 to 3 are set. In the example being illustrated, the measurement space is divided into three areas (5 blocks), and using the area 1 as the reference, the data ratio and FOV ratio of the area 2 and the area 3 are set. When these parameters are inputted, the result thereof is reflected on the measurement space of the result display part 1102. Accordingly, the user is allowed to visually check the setting result, and reentry is possible if necessary. Furthermore, it is preferable that an imaging time on which the parameter settings are reflected is immediately calculated, and the imaging time is displayed on the display part 1109.

The parameter setting screen of the present invention as shown in FIG. 11(b) is a setting screen prepared for the case where the FOV ratio is continuously changed. Similar to FIG. 11(a), this parameter setting screen is also provided with the parameter input part 1111, the result display part 1102, the imaging time display part 1109, and the like. The user sets the data ratio and the FOV ratio in the parameter input part 1111, as to the area 2 in which the FOV ratio is continuously changed, using the area 1 as the reference. A shape of the measurement space after the setting is displayed in the result display unit 1102. In this case, the echo signal obtained by the area 2 (a signal of each phase-encode) and the FOV ratio for each echo signal are automatically calculated on the basis of the inputted data ratio and FOV ratio. Simultaneously, the imaging time is calculated, and it is displayed on the imaging time display part 1109.

In FIG. 11, a setting screen for the stepwise change of the FOV ratio, and a setting screen for the continuous change thereof are independently shown. However, it is also possible to show both setting methods in one screen. By way of example, a particular numerical value or character is selected in the parameter input part 1101 (area division number) of the parameter setting screen as shown in FIG. 11(a), thereby enabling the selection of the method for continuously changing the FOV ratio. When the method is selected, the parameter input part 1106 may be allowed to have a function equivalent to the parameter input part 1111 as shown in FIG. 11(b). Alternatively, when the method of continuous changing is selected, the setting screen as shown in FIG. 11(b) may be displayed.

The configuration of the parameter setting screen is not limited to the aforementioned embodiment, and various modifications and additions are available. By way of example, the parameter input part as shown in FIG. 11(a) may be configured using a single parameter input part 1106, and it is possible to configure such that in this input part 1106, each area is selected sequentially, and the data ratio and FOV ratio are set for each area. It is further possible to provide an input part for inputting an overlap degree (upper limit value) if there is an overlapping in the FOV in the bed moving direction.

Next, a third embodiment of the readout condition control according to the present invention will be explained. FIG. 12 shows an imaging procedure of the present embodiment. In the imaging procedure shown in FIG. 12, the steps from step 411 to step 415 are identical to the steps from step 401 to step 405 as shown in FIG. 4(b). In the first and the second embodiments described above, the imaging FOV size in the readout direction is changed at the time of data measurement, according to an output amount of the phase-encode gradient magnetic field. In the present embodiment, the sampling time 305 is also changed according to the change of the imaging FOV size. With the configuration above, it is possible to obtain data having the same spatial resolution even though the FOV size is different.

In general, a data pixel pitch P is obtained by the following equation (2), based on the FOV size FOV, and matrix size Mat:

$$P = FOV \div Mat \quad (2)$$

On the other hand, the sampling time AD and the matrix size are in a proportional relationship as shown in the equation (3), if the sampling band BW is constant:

$$AD = Mat \div BW \quad (3)$$

Therefore, a pixel pitch (spatial resolution) can be kept constant by changing the sampling time AD (sampling point number) in proportion to the FOV size FOV.

Taking an example where the measurement space is divided into three, in the data measuring step 415, as shown in FIG. 5(a), in the blocks 501-1 and 501-3 for measuring the data having a high phase-encode amount, the intensity of the readout gradient magnetic field is set to be low. For example, the measurement is performed by setting the imaging FOV size in the readout direction to be twice as large as the block 501-2 for measuring the low spatial frequency component. In this case, the sampling times 504-1 and 504-3 are also made twice as long as the measurement of the low spatial frequency component as shown in FIG. 5(c), and the sampling point is also doubled. Consequently, the pixel pitch P is aligned in the blocks 501-1 and 501-3, and also in the block 501-2. Therefore, it is only required in the data reconstructing step 103 to subject the obtained data to one-dimensional Fourier transform.

According to the present embodiment, since the imaging FOV size and the sampling point in the readout direction are both changed, in response to phase-encode amount, it is possible to reduce the imaging time without reducing the spatial resolution. When the sampling point is increased, the repetition time of the sequence may be extended. However, since the unit of the sampling time is in the order of a few tens of ms, the extension of the sampling time is ignorable in the case where the sequence repetition time is long. Therefore, it is advantageous to apply the present embodiment.

In the description above, there has been explained a case where the imaging FOV size and the sampling time are changed with respect to each measuring block. As shown in FIGS. 5(b) and (d), when the imaging FOV size is changed continuously in accordance with the phase-encode amount, the sampling time 505 is also changed continuously in accordance with the change of the FOV size. Further in the present embodiment, it is possible to change the FOV size every measurement in the same phase-encode amount, or to set the FOV size so that a part of data overlaps another data. In addition, similar to the second embodiment, it is possible to control the readout condition in such a manner that the FOV size is made larger in the low spatial frequency area of the measurement space, and the FOV size is made smaller in the high spatial frequency area.

Next, a fourth embodiment of the present invention will be explained. In the present embodiment, the imaging FOV size in the readout direction is changed in accordance with the phase-encode amount, as well as changing a table position according to the imaging position. FIG. 13 shows an imaging procedure of the present embodiment. The present embodiment is different from the embodiment shown in FIG. 4a in the point that the table position change step 110 is added.

If the FOV size in the readout direction is constant, the table moving speed is set to be constant, so that the time period when the table moves in the FOV width in the readout direction corresponds to the time for measuring the data of the entire phase-encode. In the case where the FOV size is changed in response to the phase-encode amount while the table moving speed is set as described above, if the data measurement is performed with the FOV center coincident with the magnetic field center, a time is needed at the subsequent data measurement to move the table in order that the imaging FOV center matches the magnetic field center at the point where the data measurements are continuous in time wise but not continuous in the phase-encode amount. In addition, if the table moving speed is made higher in response to the reduction of the imaging time, there is a possibility that data may be missing due to the delay of the imaging. For example, in the data measurement as shown in FIG. 7(c), the sections 701-1, 701-2, 702-1, 702-2, and 702-3 are table moving time periods, until the next measurement. In this particular example, it is shown that the section 701 is longer than the sequence execution time. Therefore, in the section 701, after the data is measured, the measurement is resumed with a wait for the state where the table position is moved.

In the present embodiment, in order to prevent the extension of the imaging time due to the waiting time as described above, the next data measuring position is calculated in the table position change step 110, and before starting the next data measurement, the table is moved in forward, and then the measurement is performed. In the step 101 for setting the measuring conditions, settings of the FOV size and the measuring order with respect to each block, and the table moving speed are configured, whereby a length of the section where the phase-encode becomes discontinuous is automatically determined. Therefore, based on this length, a distance by which the table is to be moved in forward can be obtained.

In the data measuring step 102, similar to the first embodiment, only the FOV size in the readout direction may be changed. Alternatively, similar to the third embodiment, both the FOV size and the sampling time may be modified together. If only the FOV size in the readout direction is changed, in the data reconstructing step 103, a processing to make the data point number equal between the data items having different imaging sizes is executed. Steps from the table position change step 110 to the data reconstructing step 103 are repeated until reaching the end position of the imaging target range (step 104), and after the data of entire range is collected, the data arranged in the ky-x space (hybrid space) is subjected to the Fourier transform in the y-direction, for instance, thereby obtaining an image of the entire imaging target (step 105). Also in the present embodiment, as shown in FIG. 13, the image reconstruction step 105 may be performed after the data of the entire range for imaging is obtained, or the image may be reconstructed at the point of time when the data for the entire phase-encode is all acquired with respect to each FOV, and then the images of the respective FOV may be combined.

According to the present embodiment, it is possible to take an image continuously without interrupting the measurement for the table movement. Therefore, a wide FOV imaging can be performed within the minimum length of time.

Next, a fifth embodiment will be explained. In the present embodiment, the present invention is applied to a method in which imaging is performed with respect to each station while a table is moved from one station to another as to multiple stations (imaging blocks) (multi-station imaging). FIG. 14(a), FIG. 14(b), and FIG. 14(c) respectively illustrate the table positions (a) and (b), and data acquisition timing (c), in the case of the multi-station imaging.

In the multi-station imaging, as shown in FIG. 14(a) and FIG. 14(b), the table is sequentially moved to the multiple stations A, B, and C. In each station, the imaging 901-1, 901-2, and 901-3 are performed in the state where the table position is fixed. The readout direction is assumed as the table moving direction. On this occasion, as for the low spatial frequency component 501-2 having a small phase-encode amount, the data is measured in all the imaging 901-1, 901-2, and 901-3, and as for the high spatial frequency components 501-1 and 501-3, for instance as shown in FIG. 14(c), the data measurement is performed so that the FOV should be twice as large as the case where the imaging of the low spatial frequency component 501-2 is performed. In other words, as for the high spatial frequency component, the measurement is performed at the half frequency. Accordingly, the imaging time is reduced in accordance with the decrease of the measuring frequency of the high spatial frequency component.

In the case above, the data is reconstructed similar to the first embodiment, whereby it is possible to reduce the imaging time without degrading the spatial resolution, similar to the first embodiment.

Hereinabove, each embodiment of the present invention has been explained taking two-dimensional imaging as an example. However, the present invention may be applied to the multi-slice imaging or a three-dimensional imaging using a slice-encode. In the case of the multi-slice imaging, while each data items 202-1, 202-2, 202-3, and so on, of the cross sectional position 201 as shown in FIG. 2 are acquired, another cross sectional data parallel to the cross section 201 is obtained. As for the case of three-dimensional imaging, it is the same as the imaging of FIG. 2, except that each of the data items 202-1, 202-2, 202-3, and so on, includes information in the slice encoding direction. It is further to be noted that the present invention is not limited to the pulse sequence of the gradient echo system as shown in FIG. 3, and various pulse sequences may be employed.

BRIEF DESCRIPTION OF DRAWINGS

FIG. 3 includes illustrations to explain an example of pulse sequence that is employed in the moving bed imaging;

FIG. 5 includes illustrations showing examples in which an FOV size or a sampling time is changed according to a phase-encode amount;

FIG. 6 includes charts to explain a change of data readout condition in the present invention;

FIG. 8 includes illustrations to explain a data reconstruction process in the first embodiment;

FIG. 11 includes illustrations showing an example of a parameter setting screen in the MRI apparatus according to the present invention;

FIG. 14 includes illustrations showing another moving table imaging method (multi-station imaging) to which the present invention is applied, and showing an embodiment where the FOV size is changed in this method.

DENOTATION OF REFERENCE NUMERALS

Figure 1:
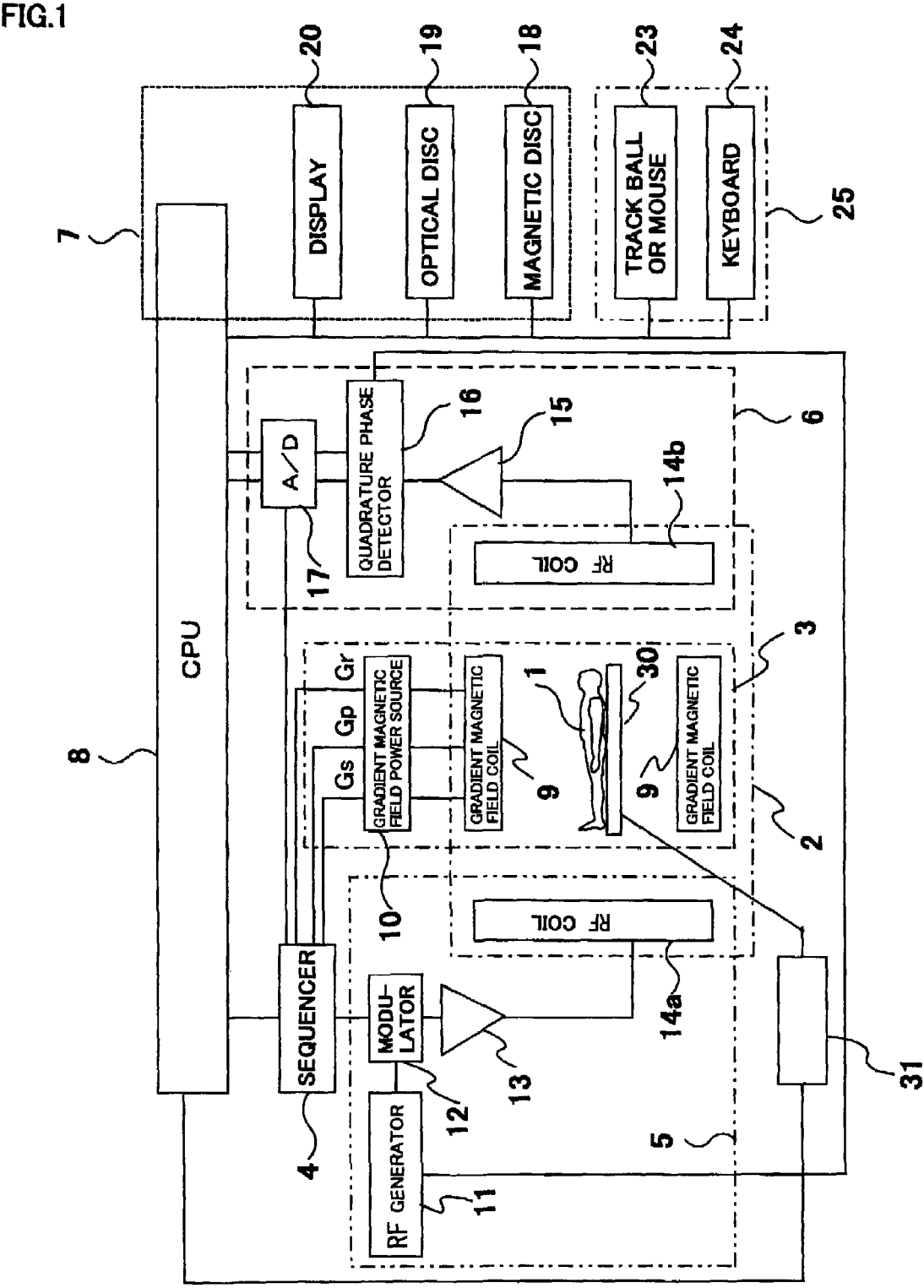
FIG. 1 is a diagram showing an overview of an MRI apparatus to which the present invention is applied.
Figure 2:
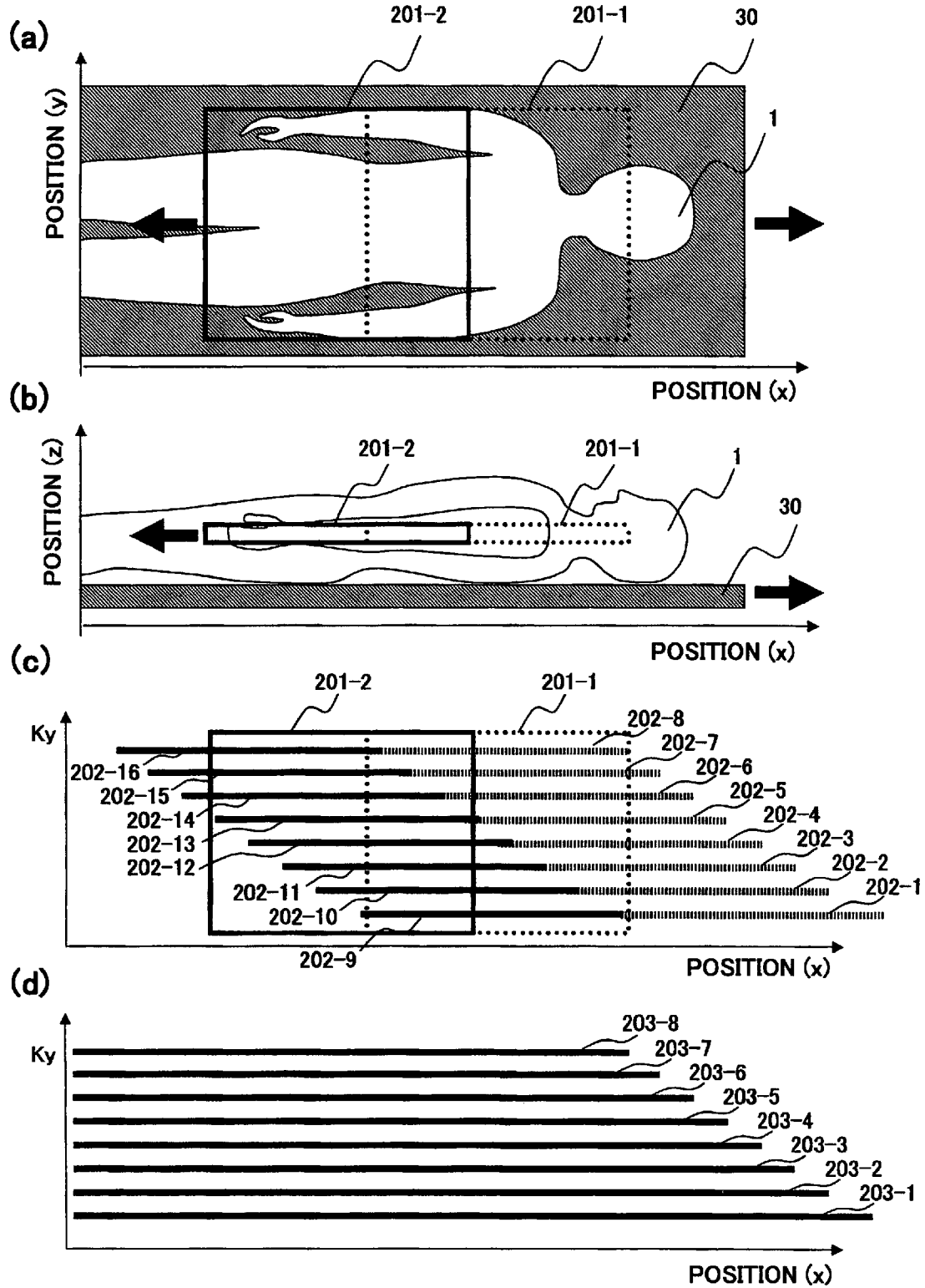
FIG. 2 includes illustrations to explain a moving bed imaging and data acquired by the imaging.
Figure 4A:
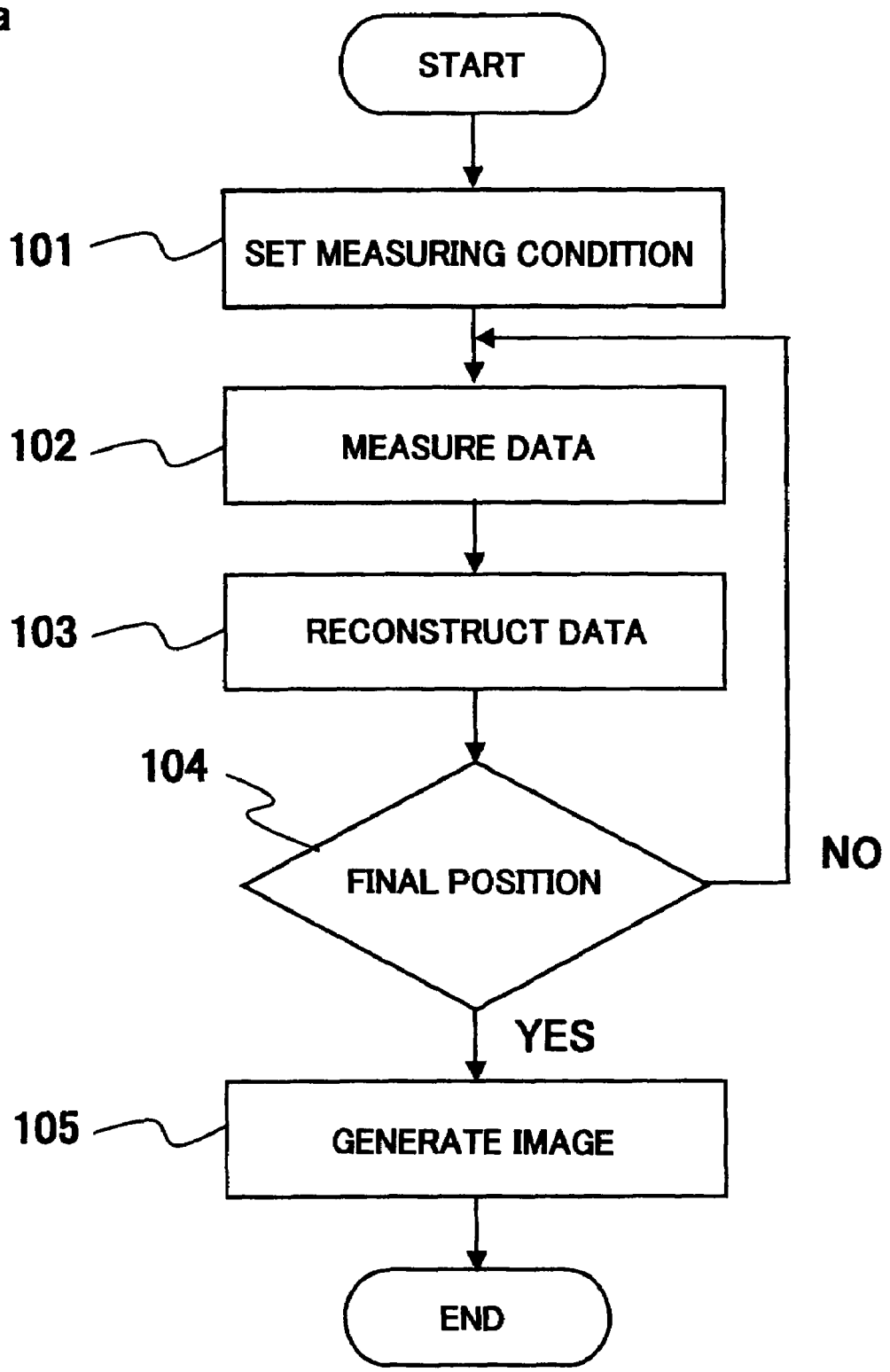
FIG. 4a is a flow diagram showing a procedure of the first embodiment of the present invention.
Figure 4B:
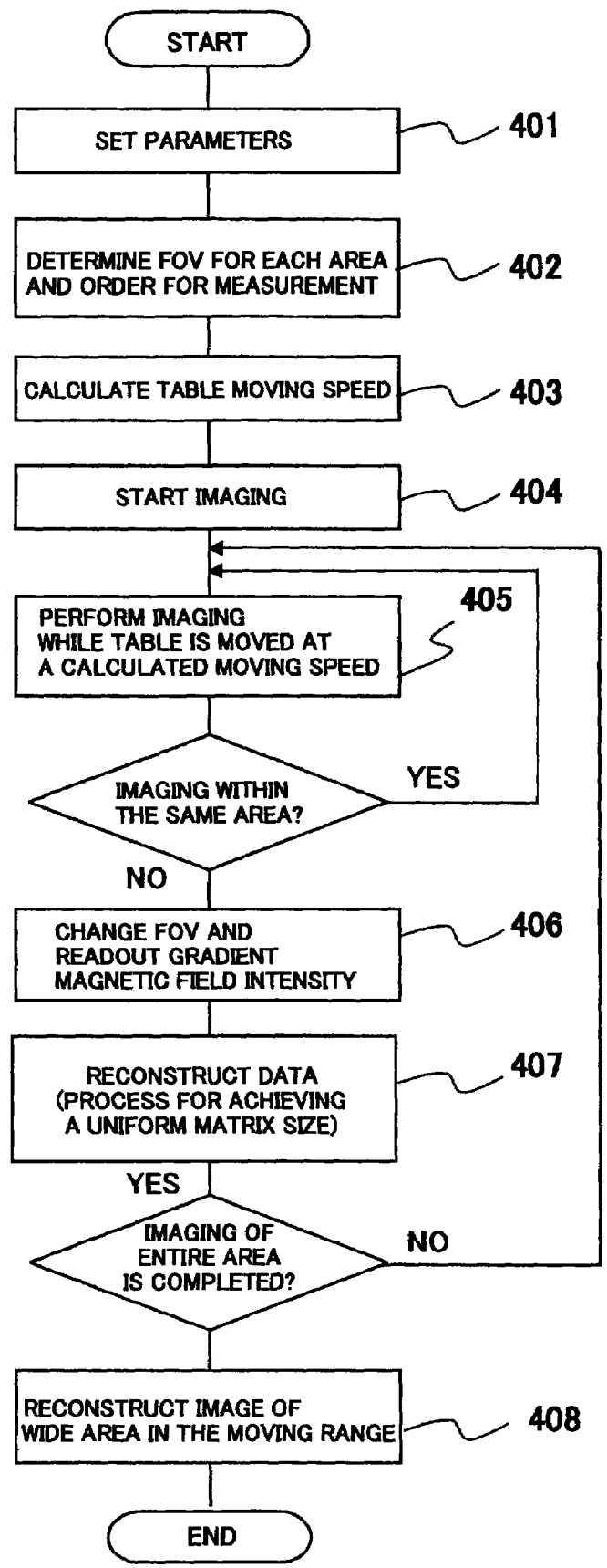
FIG. 4b is a flow diagram showing a detailed procedure of the first embodiment of the present invention.
Figure 7:
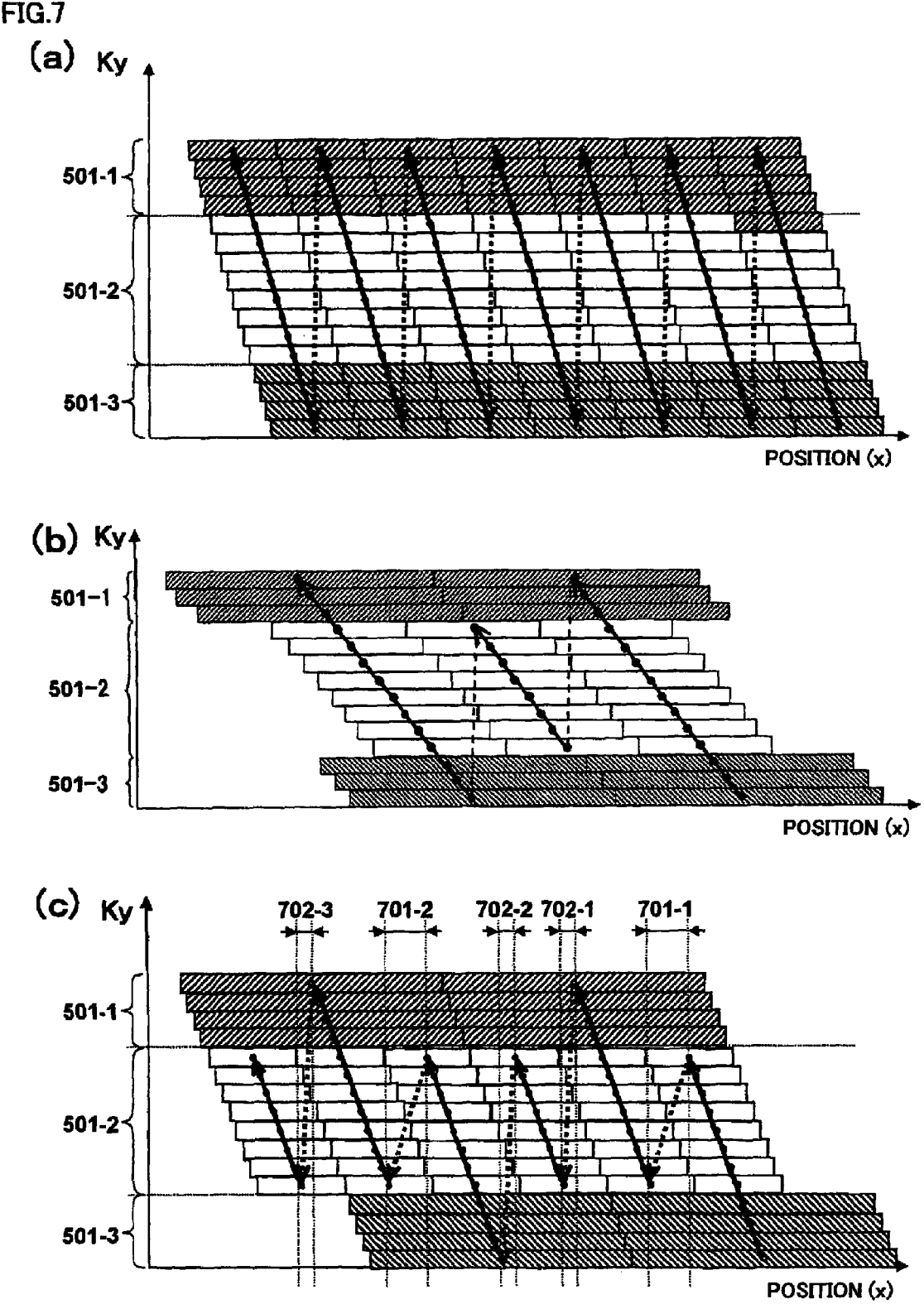
FIG. 7 includes illustrations showing an acquisition order and a hybrid spatial arrangement of the data being acquired in the continuous moving table imaging, and (a) illustrates the case where the FOV size is constant in the readout direction, and (b) and (c) illustrate the case where the FOV size is changed according to the phase-encode amount.
Figure 9:
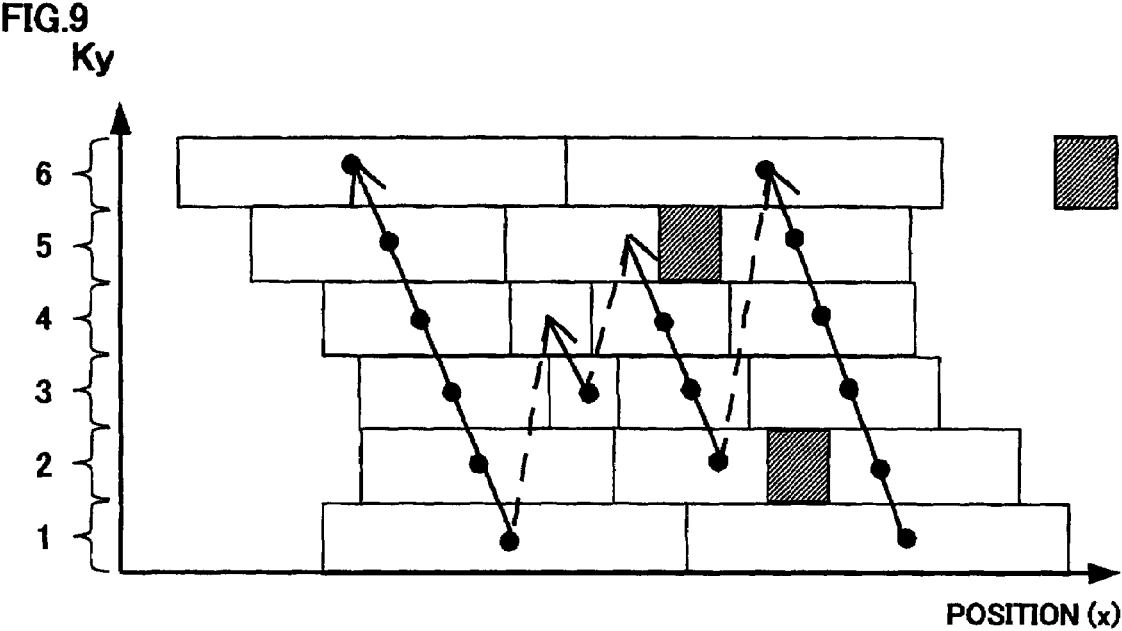
FIG. 9 is an illustration showing a modified example of the first embodiment.
Figure 10:
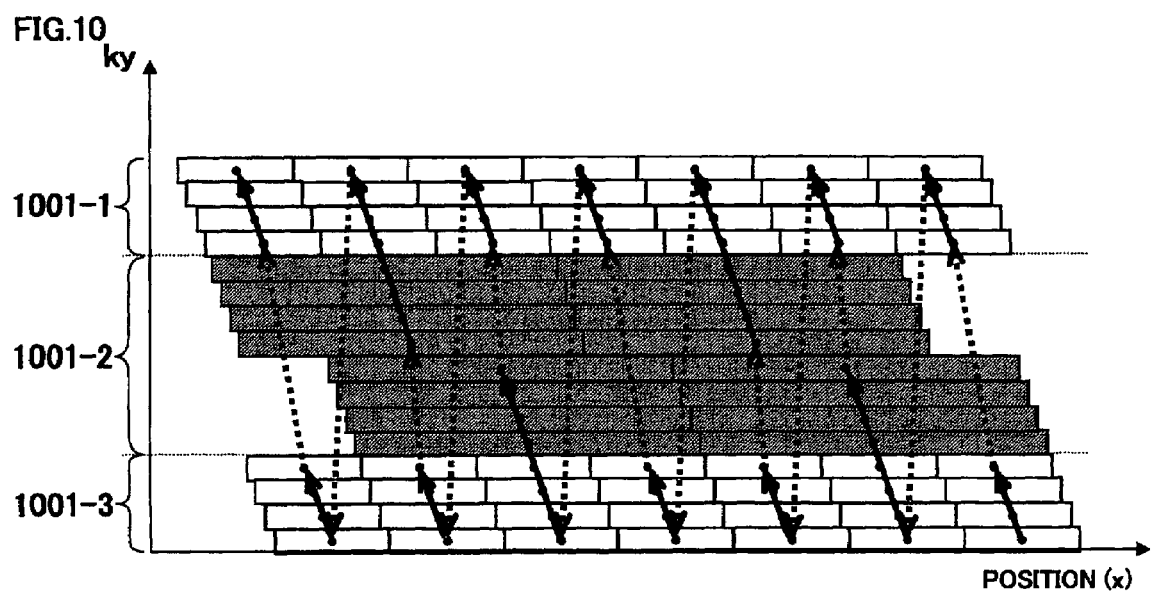
FIG. 10 is an illustration showing a measurement order in the second embodiment.
Figure 12:
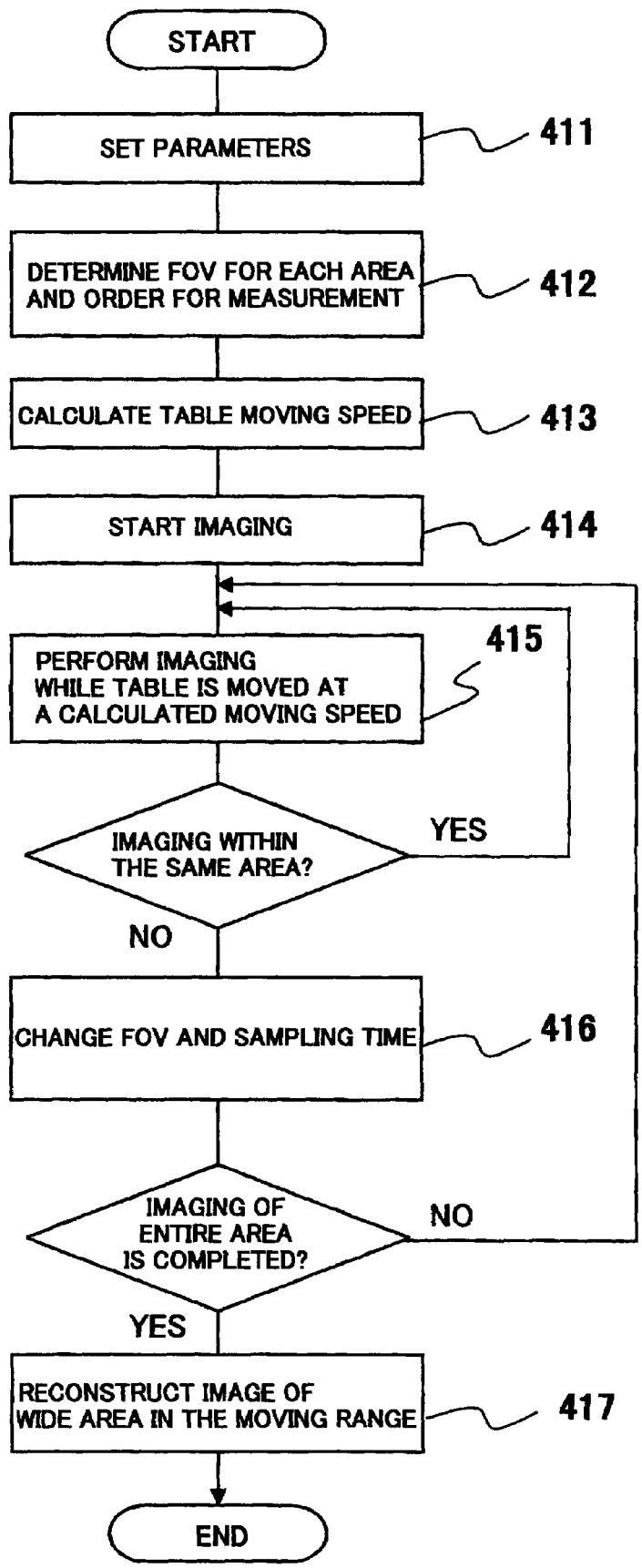
FIG. 12 is a flow diagram showing a procedure according to a third embodiment of the present invention.
Figure 13:
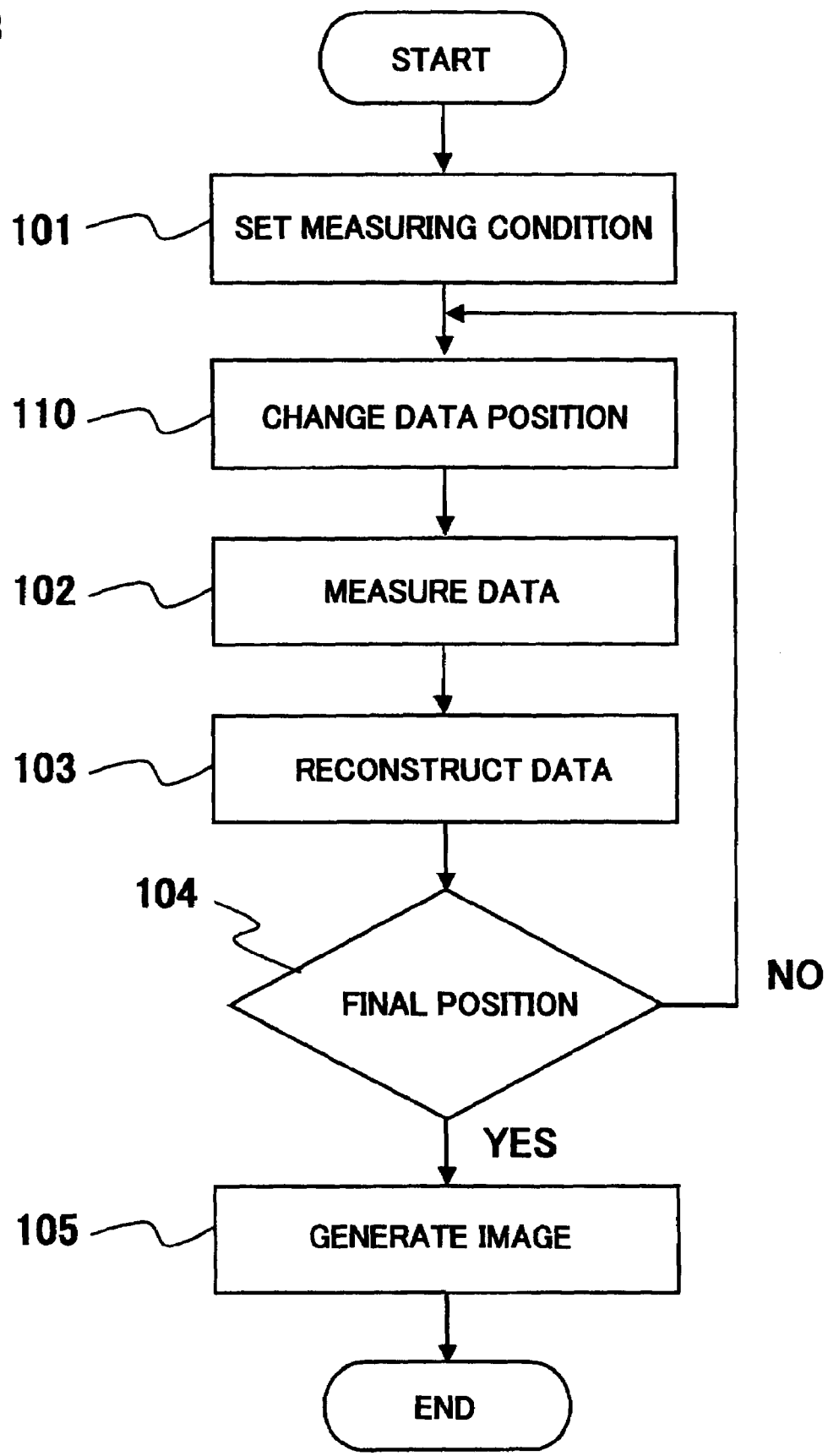
FIG. 13 is a flow diagram showing a procedure according to a fourth embodiment of the present invention.

1. TEST OBJECT, 2. STATIC MAGNETIC FIELD GENERATION UNIT, 3. GRADIENT MAGNETIC FIELD GENERATION UNIT, 4. SEQUENCER, 5. TRANSMITTING UNIT, 6. RECEIVING UNIT, 7. SIGNAL PROCESSING UNIT, 8. CPU, 30. TABLE, 31. TABLE DRIVING MECHANISM

What is claimed is:

1. A magnetic resonance imaging method comprising,
    a transfer step for moving a test object by a transfer means in such a manner that a wide imaging range of the test object passes through a static magnetic field space,
    an echo data acquisition step for performing an imaging according to a nuclear magnetic resonance and obtaining echo data corresponding to one or more phase-encode,
    a repetition step for repeating the transfer step and the echo data acquisition step, and
    an image reconstruction step for reconstructing an image of the wide imaging range by using multiple echo data items obtained in the repetition step, wherein,
    in the repetition step, a readout condition for reading out the echo data of at least one phase-encode is controlled to be different from the readout condition of the echo data of another phase-encode.

2. The magnetic resonance imaging method according to claim 1, wherein,
    in the repetition step, an FOV size in a readout direction is controlled to be different, as one of the readout condition to be controlled.

3. The magnetic resonance imaging method according to claim 2, wherein,
    in the repetition step, the FOV size for obtaining the echo data corresponding to the phase-encode in a high spatial frequency area in k-space is made larger than the FOV size for obtaining the echo data corresponding to the phase-encode in a low spatial frequency area.

4. The magnetic resonance imaging method according to claim 3, wherein,
    in the repetition step, an acquisition frequency of the echo data corresponding to the phase-encode in the high spatial frequency area in the k-space is made lower than the acquisition frequency of the echo data corresponding to the phase-encode in the low spatial frequency area.

5. The magnetic resonance imaging method according to claim 3, wherein
    a change of the readout condition according to the phase-encode is set depending on a ratio of a structure of the test object to an overall image in a reconstructed image.

6. The magnetic resonance imaging method according to claim 3, wherein
    in the repetition step, depending on the sizes of the FOV, large or small, the sampling time is extended or shortened.

7. The magnetic resonance imaging method according to claim 6, wherein,
    in the repetition step, the sampling time is controlled so that a spatial resolution in the readout direction is made approximately the same between the echo data having different readout conditions.

8. The magnetic resonance imaging method according to claim 2, wherein,
    in the repetition step, an FOV size for obtaining the echo data corresponding to the phase-encode in a high spatial frequency area in k-space is made smaller than the FOV size for obtaining the echo data corresponding to the phase-encode in a low spatial frequency area.

9. The magnetic resonance imaging method according to claim 8, wherein,
    in the repetition step, an acquisition frequency of the echo data corresponding to the phase-encode in the high spatial frequency area in the k-space is made higher than the acquisition frequency of the echo data corresponding to the phase-encode in the low spatial frequency area.

10. The magnetic resonance imaging method according to claim 1, wherein,
    in the repetition step, a sampling time in a readout direction is controlled to be different, as one of the readout condition to be controlled.

11. The magnetic resonance imaging method according to claim 1, wherein,
    in the repetition step, the readout condition of the echo data of the same phase-encode is controlled to be changed periodically.

12. The magnetic resonance imaging method according to claim 1, wherein,
    in the image reconstruction step, a matrix size in the readout direction is made equal between the echo data having different readout conditions.

13. The magnetic resonance imaging method according to claim 1, wherein,
    in the transfer step, a moving speed of the transfer means is controlled so that an FOV center for each phase-encode approximately matches a magnetic field center, in response to a change of the readout condition.

14. The magnetic resonance imaging method according to claim 1, further comprising a step for setting the readout condition prior to the transfer step.

15. A magnetic resonance imaging apparatus comprising,
    a static magnetic field generation means for generating a static magnetic field in a space where a test object is placed,
    a magnetic field generation means for generating a gradient magnetic field and a high-frequency magnetic field in the space,
    a receiving means for receiving a nuclear magnetic resonance signal generated from the test object on which a readout gradient magnetic field is applied,
    a signal processing means for performing an image reconstructing computation by using the nuclear magnetic resonance signal,
    a transfer means for placing the test object thereon and moving the test object into the space, and
    a control means for controlling operations of the magnetic field generation means, the receiving means, the signal processing means, and the transfer means,
    which MRI apparatus obtains an image of a wide imaging range of the test object by moving the transfer means, wherein,
    the control means comprises a readout condition control means that controls a readout condition of echo data to be different according to a phase-encode.

16. The magnetic resonance imaging apparatus according to claim 15, wherein,
    the readout condition control means controls application of the readout gradient magnetic field so that at least an FOV size in the readout direction is made different, as one of the readout condition.

17. The magnetic resonance imaging apparatus according to claim 16, wherein,
    the readout condition control means sets the FOV size for acquiring echo data corresponding to the phase-encode in a high spatial frequency area in k-space to be larger than the FOV size for acquiring echo data corresponding to the phase-encode in a low spatial frequency area.

18. The magnetic resonance imaging apparatus according to claim 17, wherein, the readout condition control means sets an acquisition frequency of the echo data corresponding to the phase-encode in the high spatial frequency area in the k-space, to be lower than the acquisition frequency of the echo data corresponding to the phase-encode in the low spatial frequency area.

19. The magnetic resonance imaging apparatus according to claim 15, wherein, the control means obtains an image of wide imaging range of a test object, while the transfer means continuously moves the test object, setting a moving direction as a direction for applying the readout gradient magnetic field.

20. The magnetic resonance imaging apparatus according to claim 15, wherein, the control means repeats moving the imaging area of the test object by the transfer means and, after stopping the movement, taking an image of the imaging area having been moved setting a direction for applying the readout gradient magnetic field to be the same as the moving direction.

21. The magnetic resonance imaging apparatus according to claim 15, further comprising, a means for setting the readout condition.

* * * * *